United States Patent [19]

Marker et al.

[11] Patent Number: 5,371,301

[45] Date of Patent: Dec. 6, 1994

[54] SINGLE STAGE DIISOPROPYL ETHER PROCESS USING AQUEOUS EXTRACTION AND ION EXCHANGE TREATING FOR $SO_3$ REMOVAL

[75] Inventors: Terry L. Marker, Warrenville; Laura E. Kempf, Deerfield, both of Ill.

[73] Assignee: UOP, Des Plaines, Ill.

[21] Appl. No.: 79,768

[22] Filed: Jun. 21, 1993

[51] Int. Cl.$^5$ .............................................. C07C 41/05
[52] U.S. Cl. .................................. 568/694; 568/697; 568/897; 568/699
[58] Field of Search ................ 568/694, 697, 897, 699

[56] References Cited

U.S. PATENT DOCUMENTS

| | | | |
|---|---|---|---|
| 4,182,914 | 1/1980 | Imaizumi | 568/697 |
| 4,214,107 | 7/1980 | Chang et al. | 568/897 |
| 4,499,313 | 2/1985 | Okumura et al. | 568/897 |
| 4,857,664 | 8/1989 | Huang et al. | 568/695 |
| 4,906,787 | 3/1960 | Huang et al. | 568/697 |

FOREIGN PATENT DOCUMENTS 1176620  1/1970  United Kingdom ......... C07C 41/00

Primary Examiner—Howard T. Mars
Attorney, Agent, or Firm—Thomas K. McBride; John F. Spears, Jr.; Reginald K. Taylor

[57] ABSTRACT

In a single stage process for producing diisopropyl ether, $SO_3$ from a DIPE reactor effluent is transferred to an aqueous phase in a liquid extraction zone and removed from the aqueous phase using a basic ion exchange resin disposed in an $SO_3$ removal zone. As a consequence, DIPE reactor effluent can be returned to the DIPE reactor to serve as a solvent and to assist in providing cooling to the DIPE reactor without causing catalyst deactivation.

5 Claims, 1 Drawing Sheet

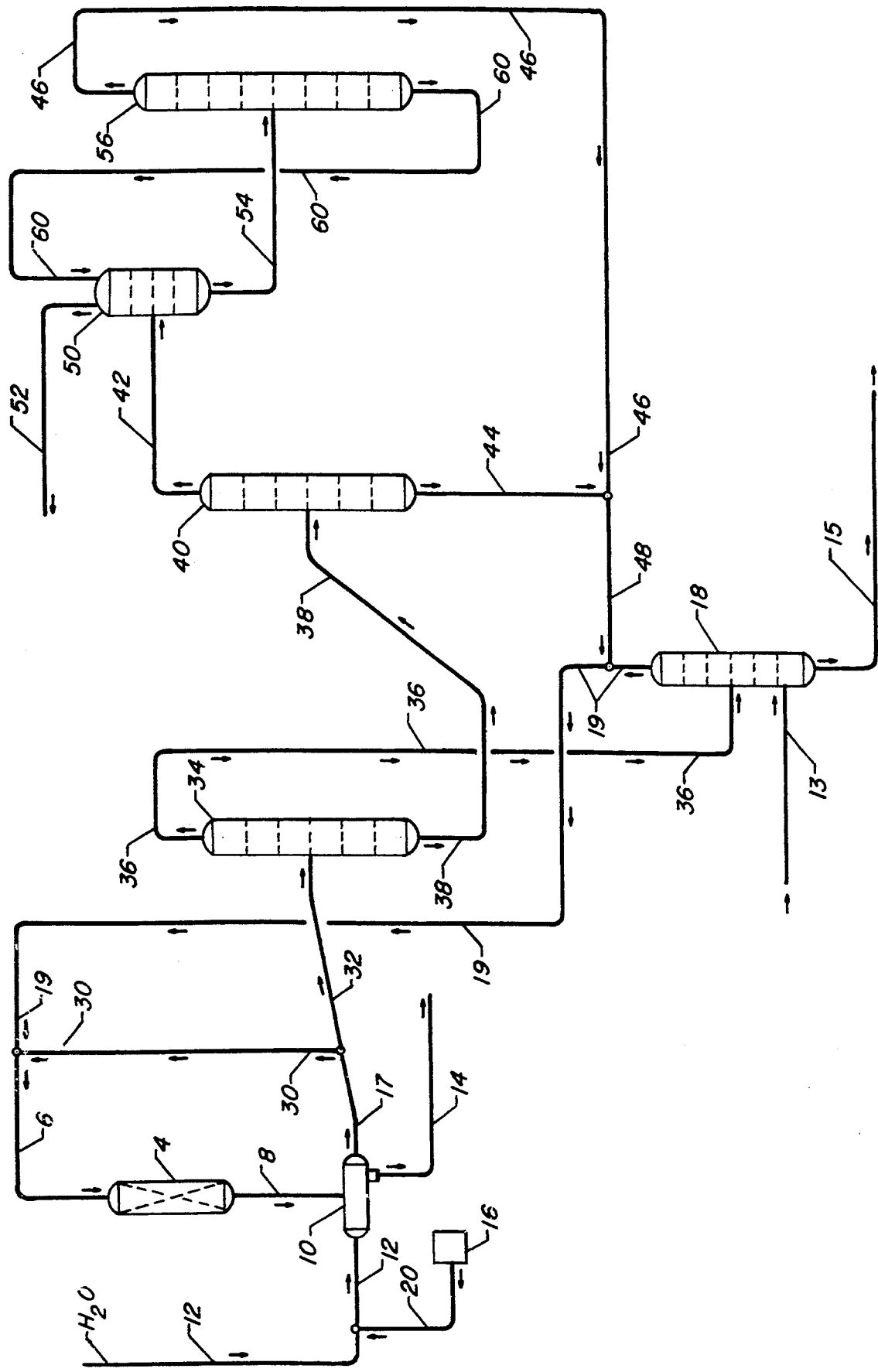

SINGLE STAGE DIISOPROPYL ETHER PROCESS USING AQUEOUS EXTRACTION AND ION EXCHANGE TREATING FOR SO₃ REMOVAL

FIELD OF THE INVENTION

The present invention relates to a single stage process for producing diisopropyl ether (DIPE) from propylene and water. More specifically, the present invention involves passing the DIPE reactor effluent into an extraction zone to transfer $SO_3$ from an organic phase comprising DIPE reactor effluent to an aqueous phase where the $SO_3$ can be removed using a base ion exchange separation process.

BACKGROUND OF THE INVENTION

The need to eliminate lead-based octane enhancers in gasoline has provided an incentive for the development of processes to produce high octane gasolines blended with lower aliphatic octane boosters. Supplementary fuels are being examined by the petroleum refining industry. Lower molecular weight alcohols and ethers, such as isopropyl alcohol (IPA) and diisopropyl ether (DIPE), are in the boiling range of gasoline fuels and are known to have a high blending octane number. They are also useful as octane enhancers. In addition, by-product propylene from which IPA and DIPE can be made is usually available in a fuels refinery, typically as a $C_3$ aliphatic stream which is rich in both propylene and propane.

The preparation of DIPE from propylene chemically proceeds by two sequential reactions where propylene is first hydrated to IPA (1) followed by reaction of the alcohol with the olefin (2) or bimolecular reaction of the alcohol (3) (Williamson synthesis) according to the equations,

(1)

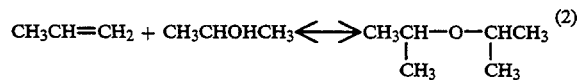
(2)

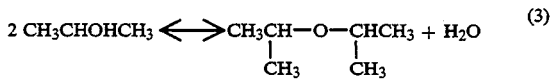
(3)

When DIPE is produced via reaction (3), twice as much IPA is required than when DIPE is produced via reaction (2). Since hydration reactions, for example reaction (1), are generally more difficult to perform than etherification reactions, the production rate of the alcohol limits the overall sequence and it is desirable to limit the formation of DIPE from reaction (3) and increase the formation of DIPE from reaction (2). Side reactions that can occur in this process are the reaction of propylene with itself to make $C_6$ olefins and the reaction of $C_6$ olefins with propylene to make $C_9$ olefins. These reactions are considered undesirable since they result in low value polygasoline with low octane and no oxygen content.

The synthetic production of IPA and DIPE is well known. Among the earliest processes for the production of IPA and DIPE were the so-called "indirect hydration processes". In the indirect hydration process, a selected olefin feed is absorbed in a concentrated sulfuric acid stream to form an extract containing the corresponding alkyl ester of the sulfuric acid. Thereafter, water is admixed with the ester-containing extract to hydrolyze the ester and to form the desired alcohol and ether which are then recovered, generally by stripping with steam or some other heating fluid. A diluted sulfuric acid stream is thereby produced. This acid stream is then generally treated to concentrate the sulfuric acid stream for recycle to the absorption stage.

In the indirect hydration process, the use of sulfuric acid as a catalyst presents certain problems. First, severe corrosion of process equipment can occur. Second, separating the produced ether from the sulfuric acid can be difficult. Third, a substantial quantity of waste sulfuric acid is produced in the concentration of the catalyst for recovery. Because of these problems, it has been found that the process of synthesizing DIPE by using concentrated sulfuric acid is not commercially desirable. Clearly, there was a need for a more direct manner of bringing about the hydration reaction.

This need was addressed by so-called "direct hydration processes" using solid catalysts. In the direct hydration process, an olefinic hydrocarbon such as propylene is reacted directly with water over a solid hydration catalyst to produce an intermediate IPA stream from which the product DIPE can be formed. Development work using direct hydration focuses on the use of solid catalysts such as active charcoal, clays, resins and zeolites. Examples of olefin hydration processes which employ zeolite catalysts as the hydration catalyst can be found in U.S. Pat. Nos. 4,214,107, 4,499,313, 4,857,664 and 4,906,787.

The use of zeolites as hydration catalysts has the disadvantage of the zeolites being expensive in comparison to other catalysts, for example, ion exchange resin catalysts. Also, in comparison to ion exchange resin catalysts, zeolites do not operate as well at the relatively low hydration and etherification temperatures where the equilibrium conversion is at its highest. Therefore, zeolites have a lower conversion per pass since the zeolites are operated at a higher temperature. In the etherification step, when no water is present zeolites have a strong tendency to form DIPE from reaction (3) instead of reaction (2). They also have a strong tendency to produce substantial amounts of undesirable polygasoline from the reaction of propylene with itself.

The use of ion exchange resins in the production of tertiary alkyl ether is well known in the art. G.B. 1,176,620 (issued to Shell) discloses reacting an olefin with an alcohol in the presence of a cation exchange resin containing an $SO_3H$ group to form a tertiary alkyl ether. The patent teaches that the preferred cation exchange resin be a sulfonated styrene/divinylbenzene co-polymer. Although sulfonated cation exchange resins have enjoyed considerable success as an etherification catalyst, these resins are susceptible to thermal degradation, by the reaction sequence shown below:

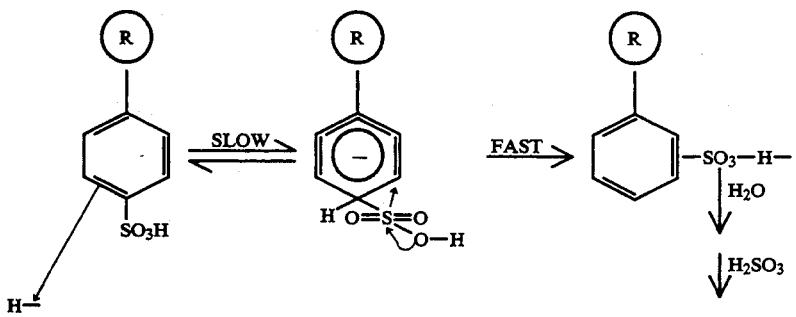

U.S. Pat. No. 4,182,914 (issued to Imaizumi) describes a two-stage process for producing DIPE using a strongly acidic ion exchange resin. Two-stage DIPE processes first make the IPA in one reactor and then react the IPA with propylene in another reactor to form DIPE. Accordingly, in a two-stage DIPE process, two reactors are required. In the Imaizumi process, propylene and isopropyl alcohol are fed to a DIPE reactor. A portion of the effluent exiting the DIPE reactor is recycled to the DIPE reactor. The remainder of the DIPE reactor effluent is passed to a neutralization zone to neutralize small amounts of $SO_3$ which is produced by thermal degradation the DIPE reactor. The neutralizing zone contains a water-insoluble, solid, particulate, acid-neutralizing agent such as magnesium oxides and aluminum oxide. The effluent from the neutralization zone is fed through a series of clean-up steps such as flashing to remove light ends and water wash to remove isopropyl alcohol.

The Imaizumi process recycles DIPE reactor effluent back to the DIPE reactor without treating the reactor effluent to remove $SO_3$. This is acceptable if $SO_3$ levels are low, i.e., when the reaction temperature is low, and when water is only present in low levels.

Two-stage DIPE processes, such as the one described in the Imaizumi patent, can be prohibitively expensive because of the capital cost associated with the two reactors. In many instances, a single stage DIPE process is more cost effective. Single stage DIPE processes can be more affordable than two-stage DIPE processes, but the single stage reactor must generally be operated at a higher temperature than the two-reactor system because water is present. As a result, the amount of $SO_3$ lost by the resin in the DIPE reactor is considerably more than in the etherification section of the two-stage DIPE process. In some circumstances, the amount of $SO_3$ in the DIPE reactor effluent can be up to 10 to 100 times as high in comparison to the two-stage process. When this high level of $SO_3$ is recycled back to the single stage DIPE reactor, the concentration of $SO_3$ in the DIPE reaction zone will increase thereby substantially accelerating the deactivation of the ion exchange resin. The reason the deactivation rate increases in the presence of the $SO_3$ is that the desulfonation rate is acid-catalyzed. Generally, the rate of desulfonation of the ion exchange catalyst increases 2.5-3.5 for every 1N increase in acid concentration.

There is a need for an economic single stage DIPE process which successfully handles the $SO_3$ catalyst deactivation problem. It is an objective of the present invention to address this need.

SUMMARY OF THE INVENTION

The objective of increasing ion exchange resin life in a DIPE process is accomplished by transferring the $SO_3$ out of the DIPE reactor effluent prior to recycling the DIPE reactor effluent to the DIPE reactor. The objective of developing an economic single stage DIPE process is accomplished by separating the $SO_3$ from the DIPE reactor effluent using an extraction zone and passing the extraction zone effluent stream to an $SO_3$ removal zone. In this manner, only a small aqueous stream is sent to the $SO_3$ removal zone rather than the entire DIPE reactor effluent stream. This results in a significant capital cost savings because the size of the $SO_3$ removal zone is significantly reduced.

The present invention is a process for the production of diisopropyl ether which process comprises the steps of: contacting a stream comprising propylene and water in a reaction zone for producing diisopropyl ether in the presence of an ion exchange resin catalyst having an $SO_3H$ functional group attached thereto under conditions sufficient to produce a diisopropyl ether reaction zone effluent stream comprising diisopropyl ether and $SO_3$; passing at least a portion of the diisopropyl ether reaction zone effluent to an extraction zone wherein the diisopropyl ether reaction zone effluent stream is admixed with water to form a raffinate stream comprising diisopropyl ether and an extract stream comprising water and $SO_3$; recycling at least a portion of the raffinate stream to the diisopropyl ether reaction zone; passing at least a portion of the extract stream to an $SO_3$ removal zone containing a basic ion exchange resin to form an $SO_3$ removal zone effluent stream; and recovering the diisopropyl ether from at least a portion of that portion of the raffinate that is not recycled to the diisopropyl ether reactor.

In one embodiment, the present invention is a process for the production of diisopropyl ether which process comprises the steps of: contacting propylene, water and recycled isopropyl alcohol in a diisopropyl ether reaction zone in the presence of a styrene/divinylbenzene co-polymer having an $SO_3H$ functional group attached thereto under conditions sufficient to produce a diisopropyl ether reaction zone effluent stream comprising diisopropyl ether, isopropyl alcohol and $SO_3$; passing at least a portion of the diisopropyl ether reaction zone effluent to an extraction zone wherein the diisopropyl ether reaction zone effluent stream is admixed with water and effluent from an $SO_3$ removal zone to form a raffinate stream comprising diisopropyl ether, propylene, and isopropyl alcohol and an extract stream comprising water, isopropyl alcohol and $SO_3$, the raffinate having a pH of less than about 3.5; recycling at least a portion of the raffinate stream to the diisopropyl ether reaction zone; passing at least a portion of the extract stream to the $SO_3$ removal zone containing a basic ion exchange resin to form an $SO_3$ removal zone effluent stream; and recovering the diisopropyl ether from at least a portion of that portion of the raffinate that is not recycled to the diisopropyl ether.

In another embodiment, the present invention is a process for the production of diisopropyl ether which process comprises the steps of: contacting propylene and water and isopropyl alcohol in a diisopropyl ether reaction zone in the presence of a styrene/divinylbenzene co-polymer having an $SO_3H$ functional group attached thereto in the presence of an added organic solvent under conditions sufficient to produce a diisopropyl ether reaction zone effluent stream comprising diisopropyl ether, isopropyl alcohol, propylene, solvent and $SO_3$; passing at least a portion of the diisopropyl ether reaction zone effluent to an extraction zone wherein the diisopropyl ether reaction zone effluent stream is admixed with water and recycled extract to form a raffinate stream comprising diisopropyl ether, propylene, isopropyl alcohol and solvent and an extract stream comprising water, isopropyl alcohol, solvent and $SO_3$, the raffinate having a pH of less than about 3.5; recycling at least a portion of the raffinate stream to the diisopropyl ether reaction zone; passing at least a portion of the extract stream to an $SO_3$ removal zone containing a basic ion exchange resin to form an $SO_3$ removal zone effluent stream; recovering the diisopropyl ether from at least portion of that portion of the raffinate that is not recycled to the diisopropyl ether; and recycling the extract stream back to the extraction zone.

BRIEF DESCRIPTION OF THE DRAWING

The FIGURE is a schematic representation of one embodiment of the present invention.

DESCRIPTION OF THE PREFERRED EMBODIMENT

In the present invention, propylene, water and recycled IPA are fed into a DIPE reaction zone in the presence of an acidic ion exchange resin catalyst under conditions sufficient to produce a DIPE reaction zone effluent stream comprising DIPE, $SO_3$, unreacted propylene and IPA.

Suitable sources for the propylene include, but are not limited to, gas plant off-gas containing propylene, naphtha cracker off-gas containing light olefins, and refinery fluidized catalytic cracked (FCC) propane/propylene streams. The concentration of propylene used will vary depending upon the source of the propylene. These sources provide a propylene/propane mixture comprising about 60–80 vol. % propylene. This mixture is passed to a propylene/propane fractionation column to increase the propylene concentration to up to about 92 vol. %. As will be discussed in more detail later, propylene recovered from downstream clean-up operations is also fed to the propylene/propane fractionation column.

The catalyst of the present invention is a synthetic ion exchange resin. The ion exchange resin of the present invention has three components: (1) the raw material which is used for the construction of the skeleton or matrix; (2) bridging agents for crosslinking and insolubilization; and (3) the type and number of functional or iongenic active groups.

With respect to forming the matrix, polymerization and polycondensation can be used as the synthesis route. Polymerization is preferred because the matrices resulting therefrom generally have higher chemical and thermal stability. The preferred starting material for synthesizing the catalyst of the present invention is styrene. The styrene is polymerized with itself and with divinylbenzene into a polymeric molecule:

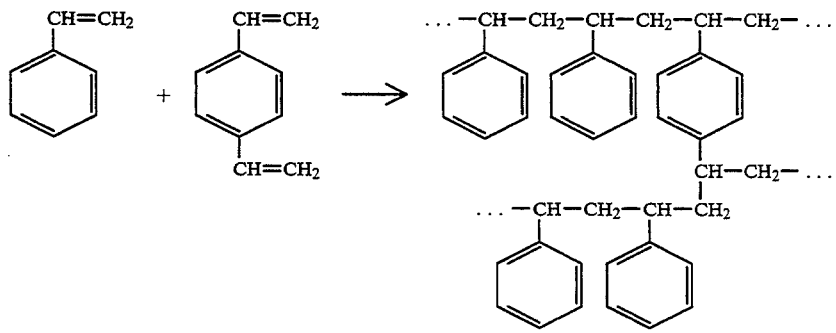

Matrices for the catalyst of the present invention can also be prepared using: (1) in divinylbenzene and acrylic acid or methacrylic acid or;

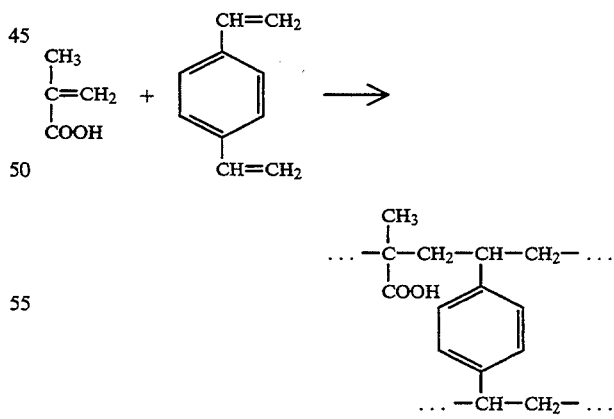

(2) phenol and formaldehyde;

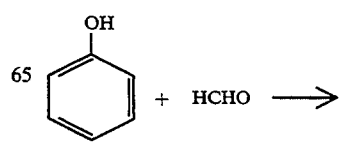

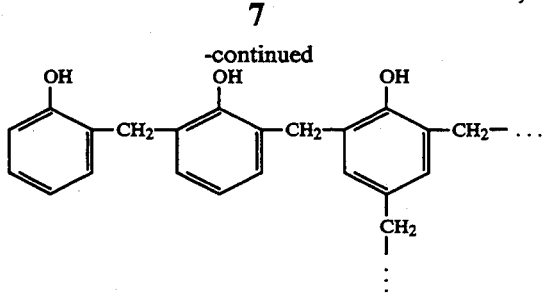

In the case of divinylbenzene-containing matrices, crosslinking depends on the quantity of divnylbenzene used as the crosslinking agent. The nature and degree of crosslinking can have a profound effect on the ion exchange properties of the catalyst. The amount of divinylbenzene used can range from about 2 to 12 wt. %. With respect to the structure of the network of synthetic resin ion exchangers, different types are now available with designations such as gel, macroporous, and isoporous ion exchange. With respect to gel-type ion exchangers, during polymerization of styrene and divinylbenzene the network formed is obtained as a gel. The properties of such co-polymer can be varied by changing the ratios of the amounts of the individual monomers used during the synthesis. These gel-type polymer structures have no appreciable porosity until they are swollen in suitable medium; but such crosslinked polymers swell to a well-defined and reproducible degree in an appropriate solvent system, such as toluene. Macroporous ion exchangers are types in which a solvent is used during production from the monomers so that a porous matrix structure is formed in the course of polymerization. The isoporous ion exchangers are a group in which the crosslinking and pore size are modified in a way to obtain polymers with a substantially uniform pore size.

In a preferred embodiment, the DIPE catalyst is a cation exchanger resin comprising $SO_3H$ groups. Suitable cation exchangers include, for example, sulfonated organic resins in their acidic form. Of particular importance are sulfonated polystyrene resins, such as the $SO_3H$ groups containing co-polymers of aromatic monovinyl compounds and aromatic polyvinyl compounds. Especially preferred cation exchangers are sulfonated styrene/divinylbenzene co-polymers, for example, "Amberlyst 36." These cation exchangers are produced by the sulfonation of suspension co-polymer beads with sulfuric acid, sulfur trioxide, fuming sulfuric acid or chlorosulfonic acid. The $SO_3$ groups which are the ionic groups yielding the cation exchange function can be in the para position.

The catalyst of the present invention can have a surface area of about 1–100 m²/g, preferably approximately 35 and a porosity of about 0.05 to 0.5 ml/g, preferably 0.30 ml/g.

Suitable conditions for the DIPE reaction zone include a temperature of about 200°–300° F., a pressure of about 100–1200 psi, preferably about 700–1000 psi, and a water to propylene ratio of about 0.1:1 to 2:1, preferably about 0.5.

In the DIPE reaction zone, etherification can be carried out under dense phase, liquid phase, vapor phase or mixed vapor-liquid phase conditions in batch or continuous manner. With respect to the etherification reactor, a stirred tank reactor or fixed bed reactor can be employed. The flow of reactants and products can be trickle-bed, liquid-upflow, liquid-downflow, countercurrent, or cocurrent, a liquid hourly space velocity of about 0.1 to 20, preferably about 0.1 to 2 when operating in the continuous mode. In a preferred embodiment, the etherification reactor can be a liquid phase fixed-bed reactor with recirculation of cooled etherification zone effluent for temperature control.

DIPE reactor effluent exits the DIPE reaction zone at a temperature of about 300° F. In accordance with the present invention, at least a portion of the DIPE reaction zone effluent stream is passed to an extraction zone. In the extraction zone, the DIPE reactor effluent stream is contacted with a water phase such that there is sufficient mixing to transfer the $SO_3$ from the DIPE reactor effluent to the water. The result is a two-phase mixture. The top phase or raffinate is organic in nature and contains a substantial amount of the DIPE, IPA, propylene and some water, hereinafter referred to as the DIPE-containing organic phase. The bottom phase or extract is aqueous in nature and contains a substantial amount of the $SO_3$, water and a small amount of IPA.

In accordance with the present invention, the extract from the extraction zone, which contains most of the $SO_3$, is passed to an $SO_3$ removal zone which contains a basic ion exchange resin. The basic ion exchange can be any one of the following types: a strong base quaternary ammonium anion exchanger; (2) a weak base anion exchanger of the amine type; or (3) an anion exchanger of the pyridine type.

Strong base quaternary ammonium ion exchangers can be obtained by the chloromethylation products of styrene-divinylbenzene co-polymers by their conversion with tertiary amines. They are easily converted from the chloride form into the OH form by treatment with NaOH. Suitable strong base quaternary ammonium anion exchangers can be prepared by conversion with trimethylamine or dimethylethanolamine. With respect to the weak base anion exchangers of the amine type, this group of synthetic ion resins comprises a complex range of products. The group includes materials with iongenic groups of primary (—$NH_2$), secondary (—NH) and tertiary amine (N) functionality, individually or in mixtures. Weak bases suitable for use as the $SO_3$ removal zone ion exchange include, but are not limited to, animated condensation products of phenol and formaldehyde: condensation products of epichlorohydrin with amines or ammonia; acrylic polymers, and amine derivatives of chloromethylated styrene-divinylbenzene co-polymers.

Operating conditions for the $SO_3$ removal zone include a temperature of about 100°–200° F. and a pressure of about 900–1100 psig.

In accordance with the present invention, at least a portion of the DIPE-containing organic phase exiting the extraction zone is recycled to the DIPE reaction zone. This DIPE-containing organic phase contains not only DIPE but also sufficient water to hydrate the propylene in the DIPE reaction zone. A suitable recycle rate ranges from 5:1 to 20:1.

That portion of the DIPE-containing organic phase that is not recycled to the DIPE reactor can be passed through several clean-up steps including light ends removal. Accordingly, in one embodiment of the present invention, the DIPE-containing organic phase is passed to a light ends fractionation zone for removal of light ends, for example. propylene and propane. The light ends fractionation zone can be operated at a temperature of about 175° F. and a pressure of about 235 psig.

The overhead from the light ends removal zone is sent to the propylene/propane fractionation column.

The bottoms stream exiting the light ends removal fractionation zone can be sent to a DIPE-IPA splitter column for removal of IPA. This splitter column is a fractionation column that separates product DIPE into the overhead and produces a stream containing IPA. The IPA-containing stream is recycled to the DIPE reaction zone where there is additional conversion to DIPE. Suitable operating conditions for the DIPE-IPA fractionation column include a temperature of about 150°–200° F. and a pressure of about 5–25 psig.

The DIPE product stream can be water washed to remove trace quantities of IPA. Accordingly, in one embodiment of the present invention the DIPE product stream is passed to a water wash zone. The water wash zone is operated at a temperature of about 50°–150° F., a pressure of about 1–10 psig, and a water to DIPE feed ratio of about 5:1 to 10:1. High DIPE product is recovered as a raffinate from the top of the water wash zone. The liquid extract containing the IPA is sent to a water-IPA fractionation column to separate the water from the IPA. An IPA-containing stream exits the water-IPA fractionation column and is recycled to the DIPE reaction zone. Water exits the bottom of the water-IPA column and is recycled to the water wash tower.

Referring to the FIGURE, a stream containing water, propylene, recycled isopropyl alcohol and DIPE is fed into a single stage DIPE reactor 4 via line 6. In the DIPE reactor 4, propylene and water react to form IPA which, in turn, reacts with additional propylene to form DIPE. Propylene enters the process through line 13 as a feed mixture of propylene and propane for propylene-propane splitter 18. A propylene-rich stream having a purity of 92% exits the top of propylene-propane splitter 18 by line 19 and is admixed with recycle stream 30 (which contains DIPE, IPA and water) to form DIPE reactor feed mixture 6. A propane-rich stream exits the bottom of propylene-propane splitter 18 through line 15. The operating conditions for propylene-propane splitter 18 are an overhead temperature of about 130° F. and a pressure of about 285 psig. With respect to DIPE reactor 4, the operating conditions include a temperature of about 300° F. and a pressure of about 1000 psig.

DIPE reactor effluent exits DIPE reactor 4 in line 8 and is passed to liquid extraction unit 10 where DIPE reactor effluent is contacted with $H_2O$ which enters liquid extraction unit 10 through line 12. In liquid extraction unit 10, $SO_3$ which is contained in the DIPE effluent stream, is transferred to the water phase via liquid/liquid extraction. Exiting liquid extraction unit 10 in stream 14 is an extract stream which contains water, IPA and $SO_3$. Extract stream 14 is cooled and passed to $SO_3$ removal unit 16 which contains a weakly basic, gel, anion exchange resin known as Amberlite ™ IRA-68 (Rohm and Haas Company). In $SO_3$ removal unit 16, $SO_3$ is removed from the extract stream by using ion exchange as the means of separation. The pH of the extract stream entering $SO_3$ removal unit 16 in line 14 is about 3.5, whereas the pH of the stream exiting $SO_3$ removal unit 14 in line 20 is as high as 6.0.

Exiting liquid extraction unit 10 in stream 17 is a raffinate stream which contains DIPE, IPA and water and which is depleted in $SO_3$. Part of the raffinate stream is recycled back to DIPE reactor 4 via line 30 to assist in cooling DIPE reactor 4. The recycle rate to feed rate is about 10:1. Since the raffinate stream is depleted in $SO_3$, the pH of the raffinate which is recycled is about 6.0.

The remainder of the raffinate from liquid extraction unit 10 is fed to light ends recovery tower 34 via line 32. In the light ends recovery tower 34, propylene and other light ends are removed in stream 36 and a stabilized DIPE-IPA stream is removed from the bottom of light ends recovery tower 34. The propylene-containing stream 36 is passed to propylene-propane splitter 18.

The DIPE-IPA stream resulting from the light ends recovery tower 34 is fractionated in the DIPE-IPA splitter 40 to separate the bulk of the IPA from the DIPE. The conditions in the DIPE-IPA splitter 40 vary from about 100° F. in the overhead DIPE-containing stream 42 to about 217° F. in the IPA bottoms stream 44. This bottoms stream 44 is admixed with a water wash fractionation column overhead stream 46 which contains IPA and the admixture is passed to DIPE reactor 4.

The overhead DIPE-containing stream 42 exits the DIPE-IPA splitter 40 and is fed to water wash tower 50. In water wash tower 50, the DIPE product is contacted with water to remove unreacted IPA. As a result of this water wash, a high purity DIPE product stream is produced in stream 52.

The extract from the water wash column is passed to water wash fractionation column 56 which separates the IPA into water wash fractionation column overhead stream 46 and recycle water stream 60. Stream 46 is admixed with stream 44 (from the DIPE-IPA splitter 40) and passed to DIPE reactor 4.

What is claimed:

1. A process for the production of diisopropyl ether which process comprises the steps of:
    (a) contacting a stream comprising propylene and water in a reaction zone for producing diisopropyl ether in the presence of an ion exchange resin catalyst having an $SO_3H$ functional group attached thereto under conditions sufficient to produce a diisopropyl ether reaction zone effluent stream comprising diisopropyl ether and $SO_3$;
    (b) passing at least a portion of said diisopropyl ether reaction zone effluent to an extraction zone wherein said diisopropyl ether reaction zone effluent stream is admixed with a stream comprising water to form a raffinate stream comprising diisopropyl ether and an extract stream comprising water and $SO_3$;
    (c) recycling at least a portion of said raffinate stream to said diisopropyl ether reaction zone;
    (d) passing at least a portion of said extract stream to an $SO_3$ removal zone containing a basic ion exchange resin to form an $SO_3$ removal zone effluent stream: and
    (e) recovering said diisopropyl ether from at least a portion of that portion of the raffinate that is not recycled to said diisopropyl ether.

2. The method of claim 1 wherein said acidic ion exchange resin comprises a styrene/divinylbenzene co-polymer.

3. The method of claim 1 wherein said basic ion exchange resin comprises a tertiary amine in a crosslinked acrylic matrix.

4. The method of claim 1 wherein said raffinate has a pH of less than about 3.5.

5. A process for the production of diisopropyl ether which process comprises the steps of:

(a) contacting propylene, water, and recycled isopropyl alcohol in a diisopropyl ether reaction zone in the presence of a styrene/divinylbenzene copolymer having an $SO_3H$ functional group attached thereto under conditions sufficient to produce a diisopropyl ether reaction zone effluent stream comprising diisopropyl ether, isopropyl alcohol, propylene and $SO_3$;
(b) passing at least a portion of said diisopropyl ether reaction zone effluent to an extraction zone wherein said diisopropyl ether reaction zone effluent stream is admixed with water and recycled extract to form a raffinate stream comprising diisopropyl ether, isopropyl alcohol, propylene and an extract stream comprising water, isopropyl alcohol and $SO_3$, said raffinate having a pH of less than about 3.5;
(c) recycling at least a portion of said raffinate stream to said diisopropyl ether reaction zone;
(d) passing at least a portion of said diisopropyl ether reaction zone effluent stream to an $SO_3$ removal zone containing a basic ion exchange resin to form an $SO_3$ removal zone effluent stream; and
(e) recovering said diisopropyl ether from at least a portion of that portion of the raffinate that is not recycled to said diisopropyl ether.

* * * * *